(12) United States Patent
Ding et al.

(10) Patent No.: US 11,530,872 B1
(45) Date of Patent: Dec. 20, 2022

(54) AIR-DRYING STORAGE DEVICE FOR CLEANED SLIDES

(71) Applicant: YUNNAN MEDICAL HEALTH COLLEGE, Kunming (CN)

(72) Inventors: Wei Ding, Kunming (CN); Hongbo Tan, Kunming (CN); Xiaotian Tan, Kunming (CN); Linyuan He, Kunming (CN); Ruopan Zhang, Kunming (CN); Qiongxian Wang, Kunming (CN); Chaofeng Hu, Kunming (CN); Fengqin Wu, Kunming (CN)

(73) Assignee: YUNNAN MEDICAL HEALTH COLLEGE, Kunming (CN)

( * ) Notice: Subject to any disclaimer, the term of this patent is extended or adjusted under 35 U.S.C. 154(b) by 0 days.

(21) Appl. No.: 17/689,871

(22) Filed: Mar. 8, 2022

(30) Foreign Application Priority Data

Jul. 15, 2021 (CN) .......................... 202110797884.8

(51) Int. Cl.
| | |
|---|---|
| *F26B 9/06* | (2006.01) |
| *F26B 5/16* | (2006.01) |
| *B01L 1/00* | (2006.01) |
| *B01L 9/00* | (2006.01) |
| *A61L 2/26* | (2006.01) |
| *A61L 2/10* | (2006.01) |

(52) U.S. Cl.
CPC ........ *F26B 9/06* (2013.01); *A61L 2/10* (2013.01); *A61L 2/26* (2013.01); *B01L 1/00* (2013.01); *B01L 9/52* (2013.01); *B01L 13/02* (2019.08); *F26B 5/16* (2013.01); *A61L 2202/11* (2013.01); *A61L 2202/23* (2013.01)

(58) Field of Classification Search
CPC .... A61L 2/10; B01L 9/52; B01L 13/02; F26B 9/06
See application file for complete search history.

(56) References Cited

U.S. PATENT DOCUMENTS

| | | | | |
|---|---|---|---|---|
| 2,623,301 A | * | 12/1952 | Weiskopf | G01N 1/312 34/202 |
| 2,852,861 A | * | 9/1958 | Jarrell | D06F 58/10 126/21 R |
| 3,683,638 A | * | 8/1972 | Devon | A61L 2/10 62/264 |

(Continued)

FOREIGN PATENT DOCUMENTS

| | | |
|---|---|---|
| CN | 111468469 A | 7/2020 |
| CN | 213463669 U | 6/2021 |

*Primary Examiner* — Timothy C Cleveland

(57) ABSTRACT

An air-drying storage device for cleaned slides, including a storage box and a slide rack; an upper right corner in the storage box is fixedly provided with a miniature air intaking pump, a lower left corner in the storage box is fixedly provided with a miniature air expelling pump; a plurality of positioning plates are arranged on left and right inner walls of the storage box; the slide rack is detachably arranged between the positioning plates; an upper end of the storage box is provided with an electric control box configured to controls entire circuit. The air expelling pump and the air expelling pump accelerate the air flow rate inside the storage box; a sealing device and a magnetic device are arranged between edges of the box doors and edges of the storage box to prevent air leakage; an ultraviolet sterilization lamp sterilize the inside of the storage box.

6 Claims, 4 Drawing Sheets

(56) References Cited

U.S. PATENT DOCUMENTS

| | | | |
|---|---|---|---|
| 3,701,201 A * | 10/1972 | Drury | F26B 9/003 392/382 |
| 2011/0167666 A1 | 7/2011 | Zoucha | |
| 2011/0167667 A1 | 7/2011 | Zoucha | |
| 2018/0193500 A1* | 7/2018 | Safavi | F26B 3/04 |

* cited by examiner

AIR-DRYING STORAGE DEVICE FOR CLEANED SLIDES

CROSS-REFERENCE TO RELATED APPLICATIONS

This application claims the benefit of priority from Chinese Patent Application No. 202110797884.8, filed on Jul. 15, 2021. The content of the aforementioned application, including any intervening amendments thereto, is incorporated herein by reference in its entirety.

TECHNICAL FIELD

The present disclosure relates to the technical field of biological section laboratory equipment, in particular to an air-drying storage device for cleaned slides.

BACKGROUND

In clinical and scientific research work, it is necessary to make pathological sections of living organs, tissues or cells taken out during surgery to determine the pathological properties and make pathological diagnosis. The used pathological slides need to be cleaned and sterilized for the next pathological analysis. After cleaning, the cleaned slides need to be completely air-dried before it can be used. However, the existing drying method for the slides is natural air-drying, the air-drying process of which is relatively long. The natural air-drying for a long time is also easy to be contaminated by variety of bacteria in the air. Therefore, it is necessary to design an air-drying device, which can accelerate the air-drying speed of the cleaned slides, and place the slides side by side on the slide rack with a small gap after cleaning. Therefore, it is also necessary to consider the ability to provide a multi-angle surround air so that the moisture between the closely spaced slides can be fully dried, and also consider the convenience of detaching the entire slide rack.

In medical experiments, it is often necessary to analyze the patient's tissue, bone marrow, blood and various secretions under microscope. In the process of making and analyzing tissue/cell slides, the samples is first stained; the stains on the slides is then rinsed with tap water after staining, and the slides are dried; then the dried slides are placed under a microscope for observation and analysis. However, in the actual operation process, there is no effective and convenient specialized air-drying device for slides. The slides can only be placed on the slide rack to dry naturally. The evaporation process of residual water spots on the slides is slow, and the natural drying time is long, which reduces the analysis efficiency of tissue/cell specimen slides. At the same time, in the process of drying, it is often contaminated by particulate dust or other impurities in the air. Therefore, an air-drying device for slides with convenient operation and high air-drying efficiency is required in the process of specimen preparation, so as to improve the air-drying efficiency of the slides.

SUMMARY

In order to solve the above technical problems, the present disclosure provides an air-drying storage device for cleaned slides. The storage device includes a slide rack, which is detachably installed between positioning plates provided on inner walls of a storage box. The slide rack is provided with a plurality of rectangular slots configured to place the cleaned slides; the storage box is provided with a miniature air intaking pump in the upper right corner and a miniature air expelling pump in the lower left corner, which can accelerate the air flow rate inside and outside the storage box and quickly dry the slides; the front side of the storage box is hingedly connected with two box doors, the edge of the box doors and the edge of the storage box are provided with a sealing device and a magnetic device that cooperate with each other to prevent air leakage which affects the air-drying effect; the upper end of the storage box is provided with an electric control box, which controls an entire circuit; the ultraviolet sterilization lamp is installed on an upper wall of the storage box, which can sterilize the inside of the storage box. The storage device is easy to operate and has a good air-drying effect; the detachable slide rack is easy to detach and install; the air intaking pump and the air expelling pump can accelerate air drying; the ultraviolet sterilization lamp can sterilize the inside of the storage device.

In order to achieve the above technical effects, the present disclosure provides the following technical solutions. An air-drying storage device for cleaned slides, comprising a storage box and a slide rack; wherein the storage box is a rectangular hollow box, an upper right corner in the storage box is fixedly provided with a miniature air intaking pump, and a lower left corner in the storage box is fixedly provided with a miniature air expelling pump; a plurality of positioning plates are arranged on left and right inner walls of the storage box; the slide rack is detachably arranged between the plurality of positioning plates; and an upper end of the storage box is provided with an electric control box.

Further, a microprocessor is arranged in the electric control box; the miniature air intaking pump, the miniature air expelling pump, an ultraviolet sterilization lamp, screen and buttons and a power supply module are electrically connected to the microprocessor.

Further, the ultraviolet sterilization lamp is installed on an upper wall of the storage box; the screen and buttons are installed on an upper surface of the electric control box.

Further, a bottom of the storage box is provided with an absorbent pad made of absorbent material, the absorbent material comprises sponge.

Further, a front side of the storage box is hingedly connected with two box doors; and a sealing device and a magnetic device that cooperates with the sealing device are arranged between edges of the box doors and edges of the storage box.

Further, the slide rack has a rectangular frame structure, and is provided with a plurality of rectangular slots downward from an upper surface of the slide rack; a depth of each rectangular slot is $\frac{1}{5}$ of a height of the cleaned slide; and an angle between each rectangular slot and a horizontal is 30 to 45 degrees.

Further, the slide rack is made of hard colorless and transparent materials, comprising acrylic plate.

Another object of the present disclosure is to provide a method of using the air-drying storage device for cleaned slides, including (1) closing box doors, turning on ultraviolet sterilization lamp through screen and buttons to sterilize inside of the storage box;

(2) detaching the slide rack, and placing the cleaned slides into rectangular slots of the slide rack in sequence;

(3) laying an absorbent pad at a bottom of the storage box;

(4) installing the slide rack between the positioning plates, and closing the box doors;

(5) setting a drying time through the screen and buttons, and then pressing a start button;

(6) pumping, by the miniature air intaking pump, outside air into the storage box; and pumping, by the miniature air expelling pump, air in the storage box to outside to accelerate air flow, so as to take away moisture on the cleaned slides and dry the cleaned slides.

The present disclosure achieves following beneficial effects.

The present disclosure provides an air-drying storage device for cleaned slides. The storage device includes a slide rack, which is detachably installed between the positioning plates provided on the inner walls of the storage box. The slide rack is provided with a plurality of rectangular slots configured to place the cleaned slides; the storage box is provided with a miniature air intaking pump in the upper right corner and a miniature air expelling pump in the lower left corner, which can accelerate the air flow rate inside and outside the storage box and quickly dry the slides; the front side of the storage box is hingedly connected with two box doors, the edge of the box doors and the edge of the storage box are provided with a sealing device and a magnetic device that cooperate with each other to prevent air leakage which affects the air-drying effect; the upper end of the storage box is provided with an electric control box, which controls an entire circuit; the ultraviolet sterilization lamp is installed on an upper wall of the storage box, which can sterilize the inside of the storage box. The storage device is easy to operate and has a good air-drying effect; the detachable slide rack is easy to detach and install; the air intaking pump and the air expelling pump can accelerate air drying; the ultraviolet sterilization lamp can sterilize the inside of the storage device.

BRIEF DESCRIPTION OF THE DRAWINGS

In order to illustrate the technical solutions of the embodiments of the present disclosure more clearly, the drawings will be briefly explained below. Obviously, the drawings are only some embodiments of the present disclosure. For those of ordinary skill in the art, other drawings can also be obtained from these drawings without any creative effort.

Figure 1:
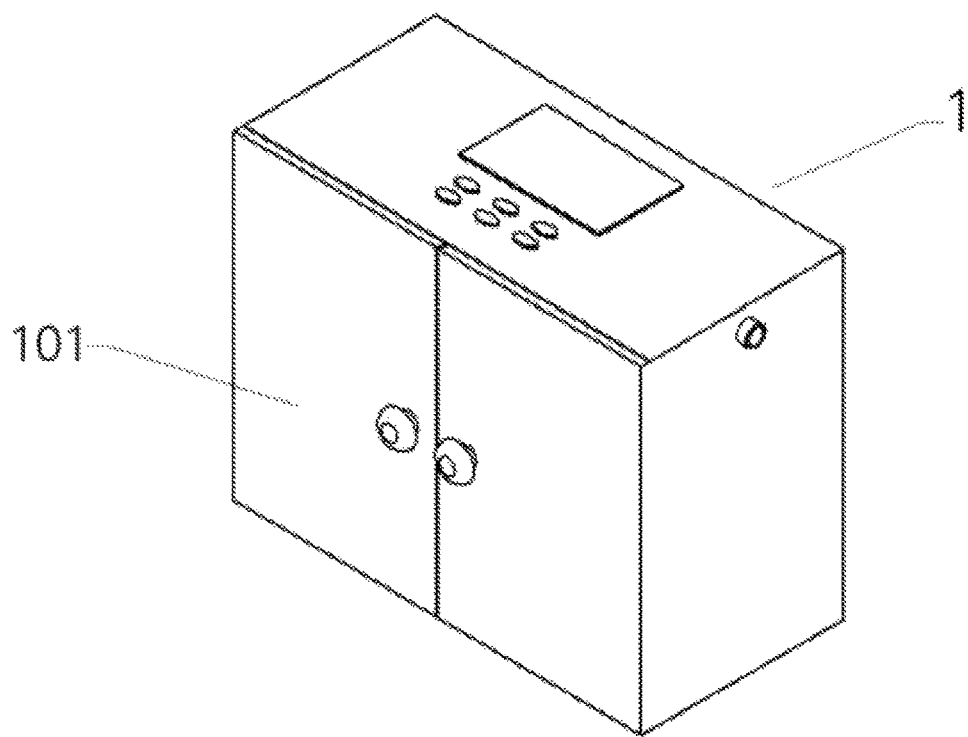
FIG. 1 is a schematic diagram of an overall structure of the present disclosure.

In the drawings, a list of components is as follows:

1, storage box; 101, box door; 102, miniature air intaking pump; 103, miniature air expelling pump; 104, positioning plate; 105, ultraviolet sterilization lamp; 106, electric control box; 107, screen and buttons; 108, power supply module; 109, microprocessor; 2, slide rack; 201, rectangular slot; 202, absorbent pad.

DETAILED DESCRIPTION OF PREFERRED EMBODIMENTS

The technical solutions in the embodiments of the present disclosure will be clearly and completely described below with reference to the accompanying drawings. Obviously, the described embodiments are only a part of the embodiments of the present disclosure, but not all of the embodiments. Based on the embodiments of the present disclosure, all other embodiments obtained by those of ordinary skill in the art without creative efforts shall fall within the protection scope of the present disclosure.

Embodiment 1

Figure 2:
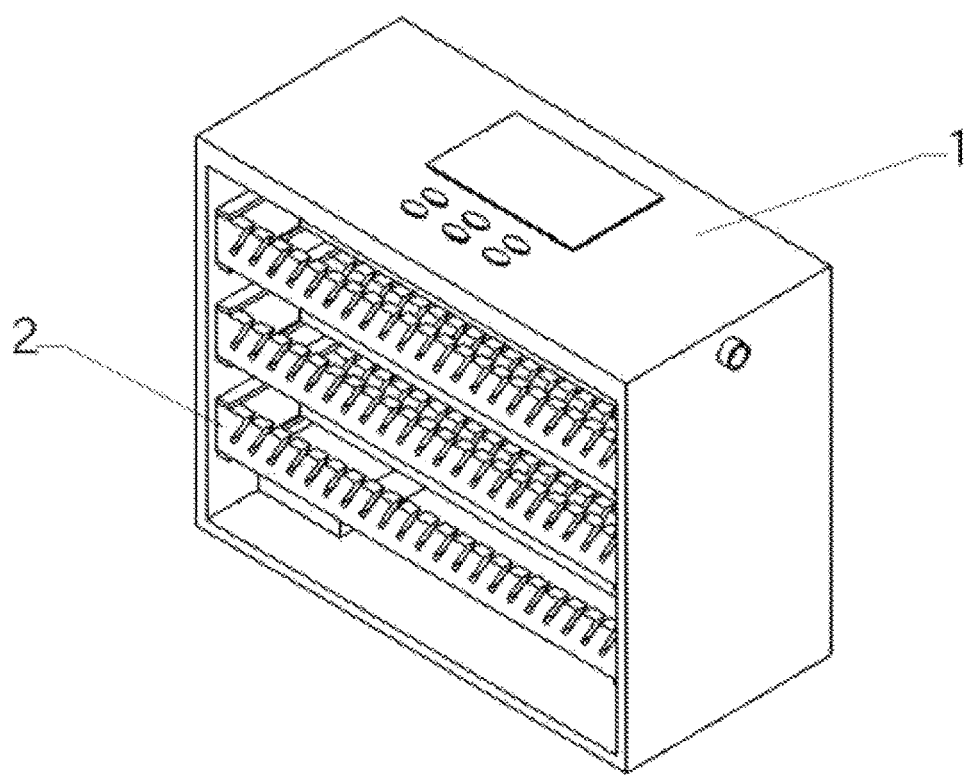
FIG. 2 is a schematic diagram of a partial structure of the present disclosure.
Figure 3:
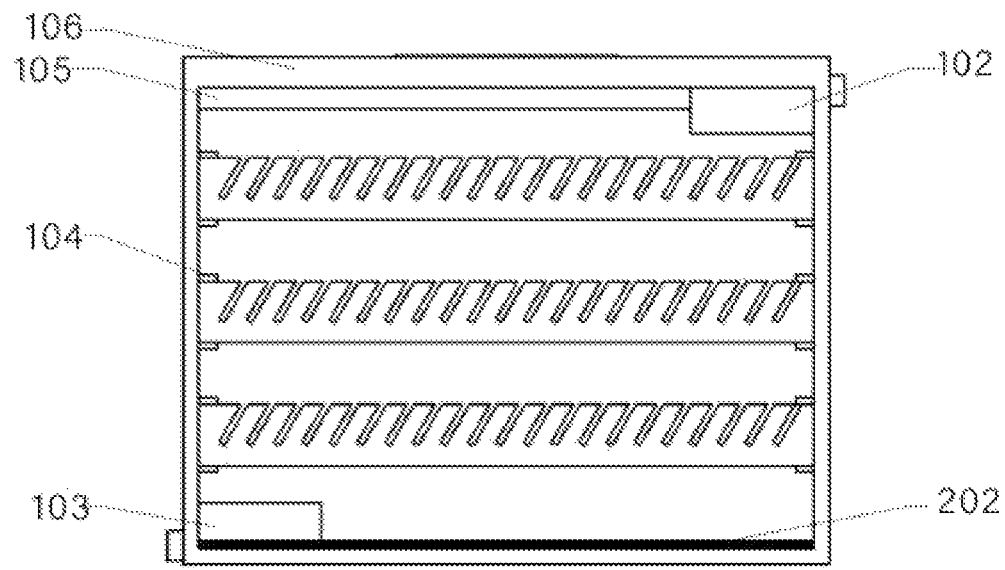
FIG. 3 is a front view of an internal structure of the present disclosure.
Figure 4:
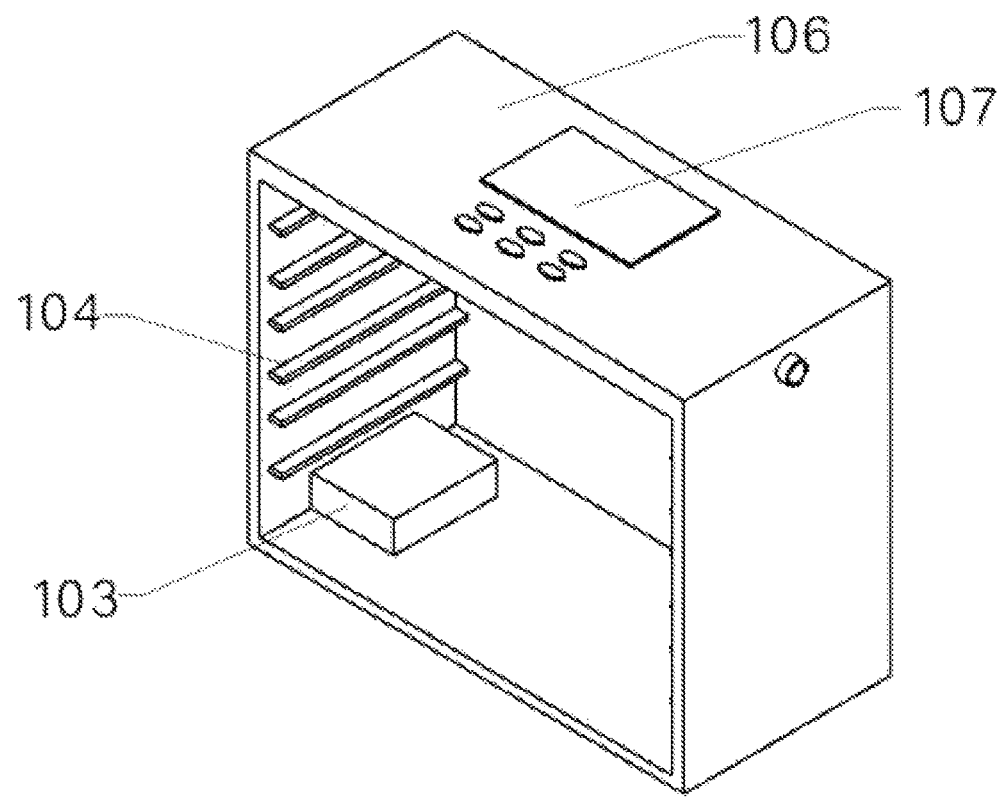
FIG. 4 is a schematic diagram of an overall structure of a storage box of the present disclosure.
Figure 5:
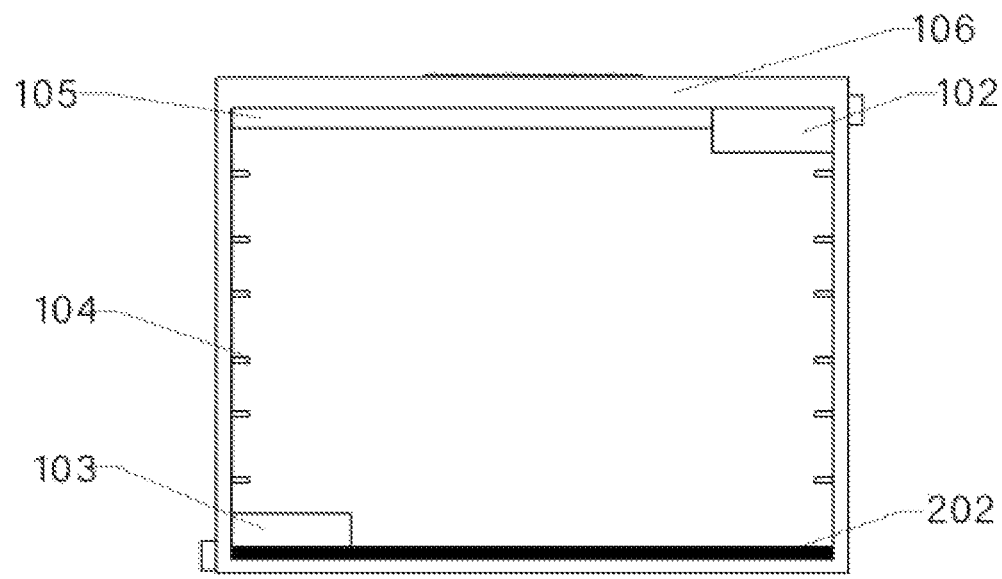
FIG. 5 is a front view of the storage box of the present disclosure.
Figure 6:
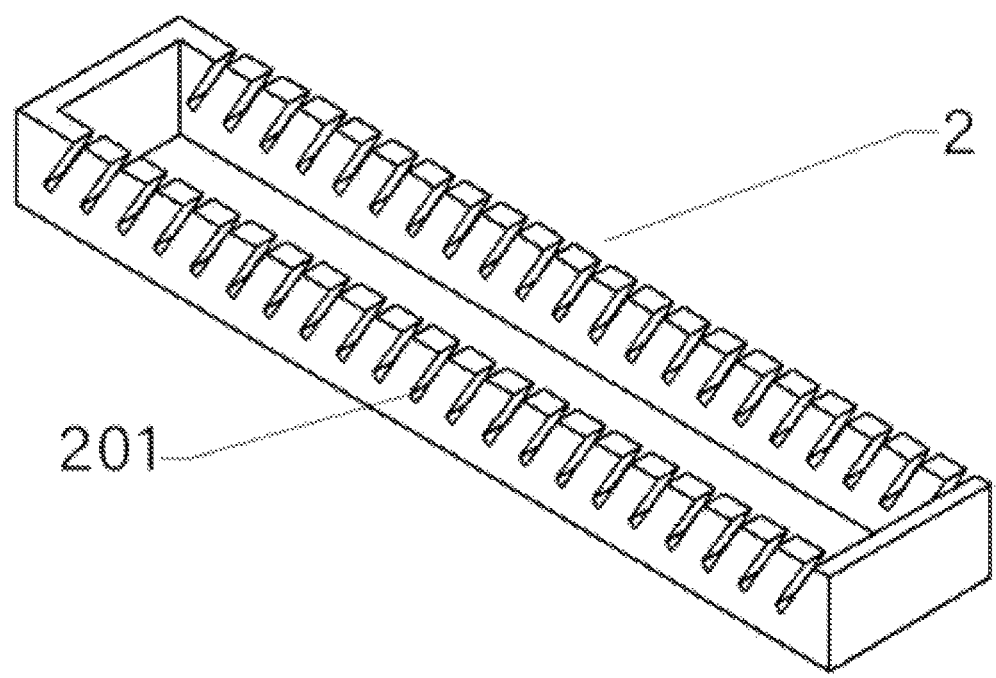
FIG. 6 is a schematic diagram of an overall structure of a slide rack of the present disclosure.
Figure 7:
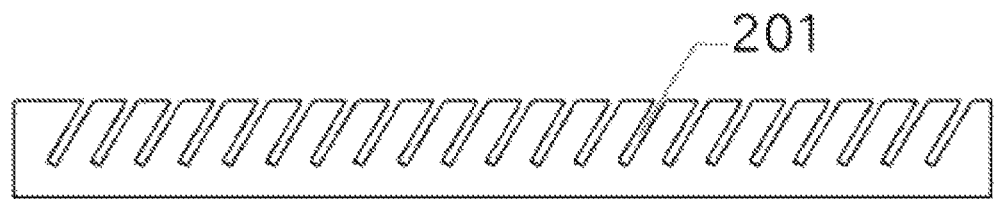
FIG. 7 is a front view of the slide rack of the present disclosure.
Figure 8:
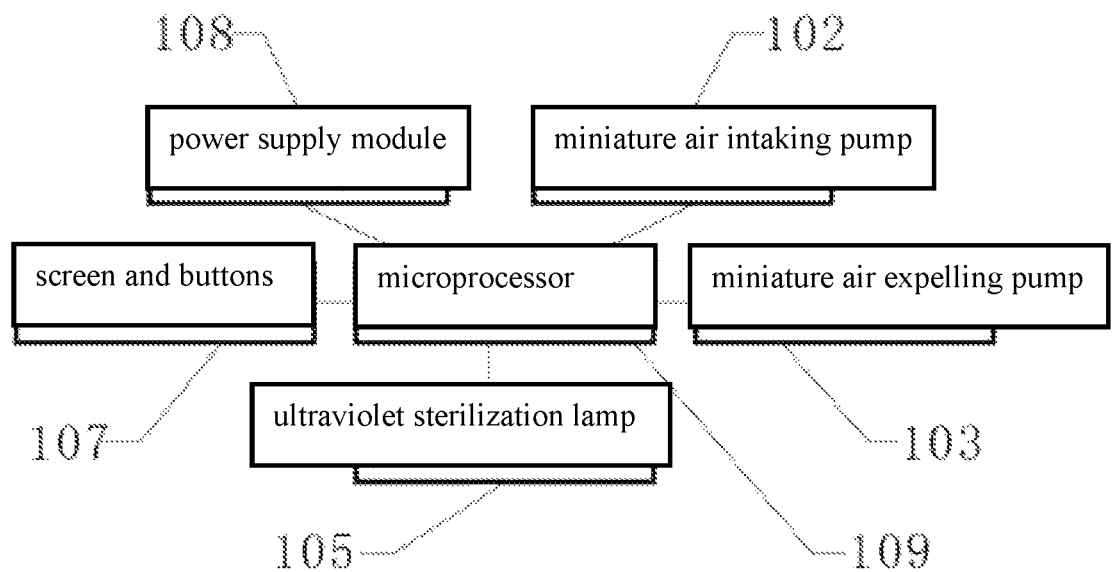
FIG. 8 is a schematic diagram of an electrical connection relationship in an electric control box of the present disclosure.

Referring to FIGS. 1 to 8, an air-drying storage device for cleaned slides, including a storage box 1 and a slide rack 2; wherein the storage box 1 is a rectangular hollow box, and an upper right corner in the storage box 1 is fixedly provided with a miniature air intaking pump 102, and a lower left corner in the storage box is fixedly provided with a miniature air expelling pump 103; a plurality of positioning plates 104 are arranged on left and right inner walls of the storage box 1; the slide rack 2 is detachably arranged between the plurality of positioning plates 104; and an upper end of the storage box 2 is provided with an electric control box 106.

A microprocessor 109 is arranged in the electric control box 1; the miniature air intaking pump 102, the miniature air expelling pump 103, an ultraviolet sterilization lamp 105, screen and buttons 107 and a power supply module 108 are electrically connected to the microprocessor 109.

The ultraviolet sterilization lamp 105 is installed on an upper wall of the storage box 1; the screen and buttons 107 are installed on an upper surface of the electric control box 106.

A bottom of the storage box 1 is provided with an absorbent pad 202 made of absorbent material, the absorbent material comprises sponge; the absorbent pad 202 is configured to absorb dripping water.

A front side of the storage box 1 is hingedly connected with two box doors 101; and a sealing device and a magnetic device that cooperates with the sealing device are arranged between edges of the box doors 101 and edges of the storage box 1 to form a sealed environment to prevent air leakage, thereby increasing drying efficiency.

The slide rack 2 has a rectangular frame structure, and is provided with a plurality of rectangular slots 201 downward from an upper surface of the slide rack 2; a depth of each rectangular slot 201 is ⅕ of a height of the cleaned slide; and an angle between each rectangular slot 201 and a horizontal is 30 to 45 degrees.

The slide rack 2 is made of hard colorless and transparent materials, comprising acrylic plate, which is convenient for irradiation by the ultraviolet sterilization lamp 105.

Embodiment 2

The present disclosure provides an air-drying storage device for cleaned slides. The storage device includes a slide rack 2, which is detachably installed between the positioning plates 104 provided on the inner walls of the storage box 1. The slide rack 2 is provided with a plurality of rectangular slots 201 configured to place the cleaned slides; the storage box 1 is provided with a miniature air intaking pump 102 in the upper right corner and a miniature air expelling pump 103 in the lower left corner, which can accelerate the air flow rate inside and outside the storage box and quickly dry the slides; the front side of the storage box 1 is hingedly connected with two box doors 101, the edge of the box doors 101 and the edge of the storage box 1 are provided with a sealing device and a magnetic device that cooperate with each other to prevent air leakage which affects the air-drying effect; the upper end of the storage box 1 is provided with an electric control box 106, which controls an entire circuit; the ultraviolet sterilization lamp 105 is installed on an upper wall of the storage box 1, which can sterilize the inside of the storage box. The storage device is easy to operate and has a good air-drying effect; the detachable slide rack is easy to detach and install; the air intaking pump and the air expelling pump can accelerate air drying; the ultraviolet sterilization lamp 105 can sterilize the inside of the storage device.

The method of using the air-drying storage device for cleaned slides is as follows: closing box doors 101, turning on ultraviolet sterilization lamp 105 through the screen and buttons 107 to sterilize inside of the storage box 1; detaching the slide rack 2, and placing the cleaned slides into rectangular slots 201 of the slide rack 2 in sequence; laying an absorbent pad 202 at a bottom of the storage box 1; installing the slide rack 2 between the positioning plates 104, and closing the box doors 101; setting a drying time through the screen and buttons 107, and then pressing a start button; pumping, by the miniature air intaking pump 102, outside air into the storage box; and pumping, by the miniature air expelling pump 103, air in the storage box to outside to accelerate air flow, so as to take away moisture on the cleaned slides and dry the cleaned slides.

In the description of the present disclosure, the terms "one embodiment", "example", "specific example", etc. mean that a particular feature, structure, material, or characteristic described in connection with the embodiment or example are included in at least one embodiment or example of the present disclosure. In present disclosure, schematic representations of the above terms do not necessarily refer to the same embodiment or example. Furthermore, the particular features, structures, materials or characteristics described may be combined in any suitable manner in any one or more embodiments or examples.

The above disclosed preferred embodiments of the present disclosure are provided only to help illustrate the present disclosure. The preferred embodiments are not specified in all details and do not limit the disclosure to the specific embodiments described. Obviously, according to the contents of the present disclosure, many modifications and changes can be made. The embodiments described in the present disclosure for the purpose of better explaining the principle and practical application of the disclosure, so that the technical personnel in the technical field can well understand and use the disclosure. The disclosure is limited by the claims and their full scope and equivalents.

The invention claimed is:

1. An air-drying storage device for cleaned slides, comprising a storage box and a slide rack; wherein the storage box is a rectangular hollow box, an upper right corner in the storage box is fixedly provided with an air intaking pump, and a lower left corner in the storage box is fixedly provided with an air expelling pump; a plurality of positioning plates are arranged on left and right inner walls of the storage box; the slide rack is detachably arranged between the plurality of positioning plates; and an upper end of the storage box is provided with an electric control box;

the slide rack has a rectangular frame structure, and is provided with a plurality of rectangular slots downward from an upper surface of the slide rack; the rectangular slots are arranged on the upper surface of opposite sides of the rectangular frame structure, allowing both ends of one of the cleaned slides to be anchored; and an angle between each rectangular slot and a horizontal is 30 to 45 degrees.

2. The air-drying storage device for cleaned slides of claim 1, wherein a microprocessor is arranged in the electric control box; the air intaking pump, the air expelling pump, an ultraviolet sterilization lamp, screen and buttons and a power supply module are electrically connected to the microprocessor.

3. The air-drying storage device for cleaned slides of claim 1, wherein an ultraviolet sterilization lamp is installed on an upper wall of the storage box; a screen and buttons are installed on an upper surface of the electric control box.

4. The air-drying storage device for cleaned slides of claim 1, wherein a bottom of the storage box is provided with an absorbent pad made of absorbent material, the absorbent material comprises sponge.

5. The air-drying storage device for cleaned slides of claim 1, wherein a front side of the storage box is hingedly connected with two box doors; and a sealing device and a magnetic device that cooperates with the sealing device are arranged between edges of the box doors and edges of the storage box.

6. The air-drying storage device for cleaned slides of claim 1, wherein the slide rack is made of acrylic plate.

* * * * *